US010622100B2

(12) United States Patent
Bremer (10) Patent No.: US 10,622,100 B2
(45) Date of Patent: Apr. 14, 2020

(54) WEB APPLICATION FOR DISTRIBUTING AND WORKING WITH CONTENTS FOR PATIENTS AND CLIENTS IN HEALTHCARE AND ELDERLY CARE. THROUGH THE WEB APPLICATION USERS CAN DISTRIBUTE CONTENT WITH POSITIVE HEALTH EFFECTS THAT PATIENTS OR CLIENTS AUTOMATICALLY AND UNASSISTED, IF NEEDED, CAN TAKE PART IN

(71) Applicant: Carl Mattias Bremer, Helsinki (FI)

(72) Inventor: Carl Mattias Bremer, Helsinki (FI)

( * ) Notice: Subject to any disclaimer, the term of this patent is extended or adjusted under 35 U.S.C. 154(b) by 120 days.

(21) Appl. No.: 14/944,502

(22) Filed: Nov. 18, 2015

(65) Prior Publication Data
US 2017/0140100 A1    May 18, 2017

(51) Int. Cl.
*G16H 10/60* (2018.01)
*G16H 80/00* (2018.01)
*G16H 40/63* (2018.01)
*G16H 20/70* (2018.01)
*G16H 50/20* (2018.01)

(52) U.S. Cl.
CPC ............ *G16H 10/60* (2018.01); *G16H 20/70* (2018.01); *G16H 40/63* (2018.01); *G16H 50/20* (2018.01); *G16H 80/00* (2018.01)

(58) Field of Classification Search
CPC .................................................... G06F 19/322
USPC ......................................................... 715/747
See application file for complete search history.

(56) References Cited

U.S. PATENT DOCUMENTS

| | | | | |
|---|---|---|---|---|
| 9,377,939 | B1* | 6/2016 | Cronin | H04L 67/10 |
| 9,700,292 | B2* | 7/2017 | Nawana | A61B 170/25 |
| 2002/0107707 | A1* | 8/2002 | Naparstek | G06F 19/3418 |
| | | | | 705/3 |
| 2002/0180803 | A1* | 12/2002 | Kaplan | H04L 29/06027 |
| | | | | 715/810 |
| 2003/0036683 | A1* | 2/2003 | Kehr | G06F 19/325 |
| | | | | 600/300 |
| 2007/0199025 | A1* | 8/2007 | Angiolillo | H04N 21/4113 |
| | | | | 725/47 |
| 2009/0037426 | A1* | 2/2009 | Haviland, Jr. | G06Q 10/10 |
| 2009/0326979 | A1* | 12/2009 | Ryan | G06F 19/3418 |
| | | | | 705/2 |
| 2010/0191037 | A1* | 7/2010 | Cohen | A61M 21/00 |
| | | | | 600/28 |
| 2010/0234671 | A1* | 9/2010 | Brandes | A61M 21/00 |
| | | | | 600/28 |
| 2010/0312042 | A1* | 12/2010 | Anderson | A61M 21/02 |
| | | | | 600/28 |
| 2011/0106557 | A1* | 5/2011 | Gazula | G06Q 10/10 |
| | | | | 705/3 |
| 2012/0150565 | A1* | 6/2012 | Gordon | G06Q 50/24 |
| | | | | 705/3 |
| 2013/0191161 | A1* | 7/2013 | Churchwell | G06F 19/3487 |
| | | | | 705/3 |
| 2013/0268282 | A1* | 10/2013 | Hugo | G06Q 50/22 |
| | | | | 705/2 |

(Continued)

*Primary Examiner* — Jason C Olson (57) ABSTRACT

The invention provides an inexpensive and natural way in today's world for a family as a whole to stay healthier and well longer and better. At the same time it supplies appropriate medical and health care material to the personnel. In addition a tool is conveniently created that can be used in many other fields of health care as well.

5 Claims, 3 Drawing Sheets

(56) References Cited

U.S. PATENT DOCUMENTS

| | | | |
|---|---|---|---|
| 2014/0081659 A1* | 3/2014 | Nawana | G16H 50/20 |
| | | | 705/3 |
| 2014/0188516 A1* | 7/2014 | Kamen | G06F 19/3406 |
| | | | 705/3 |
| 2014/0249358 A1* | 9/2014 | Brandes | G10H 1/40 |
| | | | 600/28 |
| 2015/0112724 A1* | 4/2015 | Lorsch | G06Q 50/22 |
| | | | 705/3 |
| 2015/0269355 A1* | 9/2015 | Tidor | G16H 10/20 |
| | | | 705/3 |
| 2017/0091400 A1* | 3/2017 | Richards | G06F 21/606 |
| 2017/0091464 A1* | 3/2017 | Richards | G06F 21/606 |

\* cited by examiner

WEB APPLICATION FOR DISTRIBUTING AND WORKING WITH CONTENTS FOR PATIENTS AND CLIENTS IN HEALTHCARE AND ELDERLY CARE. THROUGH THE WEB APPLICATION USERS CAN DISTRIBUTE CONTENT WITH POSITIVE HEALTH EFFECTS THAT PATIENTS OR CLIENTS AUTOMATICALLY AND UNASSISTED, IF NEEDED, CAN TAKE PART IN

REFERENCES

Art therapy and psycho-geriatric care Karen L. Drucker
Cheryl Dileo Maranto (1991) Applications of music in medicine. Washington, D.C.: National Associations for Music Therapy Publications.
Cheryl Dileo Maranto (1991) "A classification model for music in medicine", in C. D. Maranto (ed), Applications of Music in Medicine pp. 1-6. Washington, D.C.: National Association for Music Therapy, Inc.
Cheryl Dileo Maranto (1992) "A comprehensive definition of music therapy with an integrative model for music medicine" in R. Spintge and R. Droh (eds) Music Medicine. St Louis: MMB
Cheryl Dileo Maranto (1993) "'Music therapy and stress management", in R. Woolfolk and P. Lehrer (eds) Principles and Practices of Stress Management. New York: Guilford Press.
Doctor I. H. Mian, consulting psycho-geriatric at Southmead hospital district (Mian 1985)
Elokuvaterapiasta eli elävän kuvan hoidollisesta käytöstä, kirjan perustiedot 1996. Pekka Mäkipää
Halkola, Ulla 2008. Valokuvan terapeuttinen voima.
Halkola, Ulla 2009. Mitä valokuvaterapia on? Teoksessa Ulla Halkola, Lauri Mannermaa, Tarja Koffert ja Leena Koulu (toim.) Valokuvan terapeuttinen voima. Helsinki: Duodecim, 13-22.
Halkola, Ulla 2009. Symboliset valokuvat terapeutin apuvälineenä. Teoksessa Ulla Halkola, Lauri Mannermaa, Tarja Koffert ja Leena Koulu (toim.) Valokuvan terapeuttinen voima. Helsinki: Duodecim, 175-188.
Knight, B. G. (2004). Psychotherapy with older adults. Thousand Oaks, Calif.
Lee, P-L., Lan, W. & Yen, T-W. 2011. Aging Successfully: A Four-Factor Model. Educational Gerontology, 37: 210-227. Routledge: Taylor & Francis Group.
Lee, Y. & Park, K. (2008) Does physical activity moderate the association between depressive symptoms and disability in older adults? International Journal of Geriatric Psychiatry 23(3), p. 249-256.
Leino-Kilpi, H, Välimäki, M. 2009. 367 Etiikka hoitotyössä. Helsinki. WSOY.
Mannermaa, L. 2000. Uusia tapoja katsoa ja tuntea, nähdä ja oivaltaa. Teoksessa: Mieli ja taide (toim.) Heikkilä, T., Paloheimo, L. & Taipale, I. Vantaa: Printway Oy. 61-64
Mielenterveys vanhuudessa 2012, Sirkkaliisa Heimo, Hannu Pajunen; Yleistä ikääntymisessä Saarenheimo Marja; Ikääntyneiden Psykoterapeuttisen Työn Puitteista ja Lähtökohdista Hannu Pajunen; Vanhuksen Psykodynaaminen Psykoterapia Pirkko Siltala; Kognitiivinen Psykoterapia Ikäihmisten Mielialaongelmien Hoidossa Marja Saarenheimo; Interpersoonallinen Psykoterapia ja Neuvonta Jarmo Kontunen; Vanhusten Perheterapia Hilkka Virtanen; Ryhmätoiminnan Mandollisuuksista Susan Kuusisto & Ari Marjovuo & Riikka Salmi & Irene Tummavuori; Kognitiiviset Toiminnot—Kuntoutuksen ja Tuen Mandollisuudet Normaalissa Ikääntymisessä ja Muistisairauksissa Tuomo Hänninen & Sirkkaliisa Heimonen; Mielenterveyttä Kaiken Ikää Hannu Pajunen.
Music Therapy in Health and Education 1999. Margaret Heal, Tony Wigram
Musiikkipsykoterapia Teoria ja käytäntö Oulun yliopisto 2014. Sami Alanne
Psychologists' Use of Motion Pictures in Clinical Practice Georgios K. Lampropoulos Ball State University Nikolaos Kazantzis Massey University and Waitemata District Health Board Cognitive Therapy Center Frank P. Deane University of Wollongong
Punkanen, T. 2001. Mielenterveystyö ammattina. 2-5. painos. Helsinki: Tammi. 9-10.
Saarenheimo, M. 2003. Vanhuus ja mielenterveys. Vantaa: Dark Oy, 90-94.
Uudistuva mielenterveys työ, Maria Vuorilehto, Tuulevi Larri, Marjo Kurki ja Heli Hätönen
Virtanen, H. (1991). Vanhusten perhe-ja ympäristökeskeinen psykiatrinen hoito. Turku University publications, series C: Scripta Lingua Fennia Edita: 85.
Winblad, I. 2007. Vanhusten psyykkiset häiriöt. Viitattu Dec. 29, 2013
http://therapiafennica.fi/wiki/index.php?title= Vanhusten_psyykkiset¬_h%C3%A4iri%C3%B6t.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Depression, low self-worth, disorientation, marginalization, unresolved problems or disputes, paranoia, grief, jealousy, interaction problems, memory loss, speech topics and passing time are some of the problems facing elderly clients in home and elderly care today. The same problems are faced by clients hospitalized as well as those associated with health care in other ways. (Uudistuva mielenterveys työ, Maria Vuorilehto, Tuulevi Larri, Marjo Kurki ja Heli Hätönen, Vanhusten perheterapia, Hilkka Virtanen) My own experiences from elderly care especially communication with the help of different content, extensive field trips and research in a health care and hospital environments have contributed to this invention. Also discussions with elderly care institutions and with other comparables about existing products and need accompanied by the many budgetary constraints of today has formed this product.

Going through the clients or patients life cycle is very beneficial in therapy for the elderly. When going through the life cycle family members can relate the client's current problems to problems in the past. The family members can be activated to use similar methods in the present situation to those found beneficial in the past. Elderly people can better realize the value and meaning of their life. The life cycle also presents a constructive way of going through unresolved prior problems. The following situations in particular are useful to be treated with a life cycle approach: Depression of an elderly where the life cycle is used to outline her life's meaning and value also in relation to the family. Grief related to somatic illness of a partner. In dealing with the common grief and in preparation for the future. A paranoia that has started at an older age. In communication and interaction problems between the patient or client and her adult children. The life cycle view constructively helps with the fundamental problems at the root of the interaction problems. The same methods are used in family therapy for the elderly as in family therapy overall, cultural differences considered of course.

All family therapy techniques are applicable to elderly care as well. Therefore it is very beneficial that many techniques can be applied. Especially a family oriented approach can be useful. This can be helpful for younger members later when reflecting on things. The focus is thus adapting to the situation, supporting family members or changes in the inner dynamics of the family. The goals can be divided into 5 categories: Treating current interaction problems in the family or bettering interaction. Helping the family deal with the difficult situation. Dementia does not hinder the treatment. Helping the elderly view their life as meaningful, valuable and important. In executing preventive psychiatric work for the family members. This can pertain to a family living in the same household but also in families far apart, between siblings and where the elderly is institutionalized. The therapy can consist of simple interaction or a situation where the family is encouraged to actively take part in the different phases of the treatment.

Music therapy has advanced especially in the US during the past 15 years. In music therapy both the music and the therapeutic relationship to the patient are essential. (Dileo-Maranto 1991, 1992, 1993) I.e. it is important to have a good relationship and know the patient well also music vise. Medical goals of music therapy can be summarized in the following way: Relieving stress and agitation, relieving pain, relieving depression, helplessness, and bettering the immune function. Pain relief and diverting the patient's attention elsewhere can aid the healing process. The reduction of typical emotions that are linked to sickness like depression, helplessness, isolation, withdrawal, losing control and so on can be physiologically beneficial to the patient. Through research it has also been found that one by listening to music has been able to improve a part of the immune function. (Maranto 1993) Some common points in relation to music therapy and other therapy from the literature. Firstly it seems that music has the ability to affect individuals' bio medically and psycho-socially at the same time. Thus it seems as music is a particularly effective and immediate form of treatment for medical illnesses. Secondly, music unlike other medical interventions does not hurt or inflict pain on the patient. Thirdly, contraindications for using music are small and side effects at most small. Fourth, music is easy to use for the patient both as a treatment and in home care. It allows the patient to slightly take control of her treatment and be part of it. And lastly the cost effect relationship is good in relation to sky high costs of other medical intervention. (Maranto 1992, 1993) Below are uses for music from the research literature: Music awakens physiological reactions and is a complex stimulus. Music provokes psychological reactions. Music evokes images and associations and can drive a little bit the same thing as images and pictures. They can work together especially as the patient or client is well known. Music raises cognitive reactions. These reactions may be important for the effectiveness of therapeutic intervention. Music can cause physiological and/or psychological resonance. This is stated as a physics process in research. Physiological, psychological and cognitive reactions to music are individual. It is thus important to know the patient or client.

The musical uses in medicine are many I will list the sectors here to give an overview: Music in surgery: Is good for lowering stress, restlessness, blood pressure, speeds up healing etc. Music in the Neonatal Intensive Care Department: positive and calming effects. Music in pediatric care: reduces anxiety and stress. Music in physical rehabilitation: Is good for rhythmic movements, improves motoric ability, reduces tension and motivates. Music in treating respiratory disease: resonates breathing, improves breathing and relieves restlessness. Music in treating burns: alleviates pain, reduces heart beat during procedure and reduces psychological trauma etc. Music in pain relief: impacts psychological and physiological aspects, increases calm, increases the pain threshold and reduces the need for pain medication. Music in stress relief: reduces muscle tension, psychological anxiety, blood pressure and is calming overall. Music in general hospital or intensive care: reduces anxiety, alleviates pain, increases the feeling of wellbeing, calming, entertaining and betters the mood. Music during labor: reduces fear and anxiety, controls breathing, shortens the process and is positive and soothing for everyone involved. Music in oncology and terminal care: alleviates pain, presents opportunity to draw attention away from disease, alleviates talking about the disease, reduces restlessness, offers some control/reduces helplessness, helps the patient deal with sickness and death and helps the family with things regarding the patient.

Combining music with therapy and with pictures and movies is very appropriate. Aristoteles of Greece wrote about the cleansing properties of music and art. In Finland the University of Helsinki found that music listeners rehabilitated faster, music was found to calm patients and familiar music was found to alleviate psychological stress and to raise patients' mood. Music worked well with normal choirs' as well raising thoughts, images and stimulating the brain. Less depression and disorientation was found among patients receiving music rehabilitation. This was also studied in relation to elderly care. As was found in the previous, music has many positive effects. (Musiikkipsykoterapia Teoria ja käytäntö Oulun yliopisto 2014. Sami Alanne)

Picture and movie therapy is based on basically 4 factors: Identification, the need to relate to the characters, the environment and form a sufficient emotional connection. Projection, the need to reflect on the characters or through them, different usually powerful emotions. Imitation, the need to replicate and mimic characters appearance for learning and values in one's own life. Idealization, the need to get or create ideals, authority figures and role models. Movies are very suitable to therapeutic work to which especially home movies are counted. This can work over a longer or shorter period of time and is good in forming patient/client interaction. All kinds of personalities can watch recordings alone or together for personal fulfillment and approval. This is also good for group dynamics. Self-searching and documentation is also an effective form of movie therapy. A recording can even be added to the medical history. In picture, art, music, dance, literature and drama therapy movies can work as an effective addition or documenter. Using movies as a form of therapy requires a good knowledge of the client. With a movie one can create many associations to the client, her feelings, and handled topics within a group and its member's events and turns of life drawing the client closer. With pictures, movies and sound art can be created. A bridge can be formed between the therapist and the client. (Elokuvaterapiasta eli elävän kuvan hoidollisesta käytöstä, kirjan perustiedot 1996. Pekka Mäkipää)

Do professional psychologists use motion pictures in clinical practice? If so, do they consider motion pictures to have therapeutic value? Of 827 licensed practicing psychologists, 67% reported the use of motion pictures to promote therapy gains. Most of these practitioners (88%) considered the use of motion pictures as effective in promoting treatment outcome, and only a minority (1%) reported them as potentially harmful. Compared with their psychodynamic counterparts, therapists practicing within eclectic-integrative, cognitive-behavioral, or humanistic frameworks were more likely to view or use motion pictures as therapeutic tools. Psychologists provided individual evaluations of 27 motion pictures that deal with a variety of mental health subjects, and overall they were characterized as "moderately helpful." (Psychologists' Use of Motion Pictures in Clinical Practice Georgios K. Lampropoulos Ball State University Nikolaos Kazantzis Massey University and Waitemata District Health Board Cognitive Therapy Center Frank P. Deane University of Wollongong)

(Increasing Family Involvement in Elderly Care HAN University of Applied Sciences Department of Information Technology, Communication and Media Ruitenberglaan 26, 6826 CC Arnhem, The Netherlands 7.2014.) This paper describes the design and field trial of the Dynamic Collage, a system which aims support extended family members to take part in the care for an elderly person in a light way manner by sending photos to a digital frame in the elderly home. We evaluated the dynamic collage in a field trial of 4-6 weeks with two families, yielding positive results. Photo-sharing was seen as a valuable contribution by the elderly person and all family members, it provided narrative support for visitors of the elderly and it led to an increased awareness of caregiving behavior and increased cohesion in the family. The study shows there is an opportunity to include Awareness Systems and Persuasive Technology within a participation ecology, which could be beneficial for health care (Art therapy and psycho-geriatric care Karen L. Drucker) The writer concentrates on psycho-geriatric care in general hospitals and other services offered to elderly people. In connection to e.g. depression, phobias, nervousness and mild states of confusion. Doctor I. H. Mian, consulting psycho-geriatric at Southmead hospital district (Mian 1985) has stated that the main principals of the services are: Early right assessment at home, Interdisciplinary teamwork, Cooperation with other forms of service, Support for relatives and other professional helpers, Contacts with voluntary organizations, The training and attitude formation of the general public and the medical staff, Research. Mrs. Drucker has worked as a therapist in 3 day hospitals. She now focuses on treating people suffering from depression and grief gusts. Art therapy has had a positive impact on remembering, life-cycle viewing and defining the current states pros and cons. She usually deals with ordinary themes like weddings, children, family tree and other surfaced events. Art therapy is seen as a useful escape for which there has not been room for before with the demands of everyday life with no room for "creative "or" human growth". It is important for elderly people to remember and organize events from the past life. People suffering from dementia have a harder time concentrating making for example drawing harder. Making films, taking pictures, recording and writing can also be included in therapy. Mrs. Drucker uses these methods at day hospital and in outpatient groups. Today's technology provides many new and easier forms of expression. She also emphasizes the importance of preventive care in the treatment of the elderly. This can be treated with preventive therapy.

The most common disorders of the mind among elderly people are depression, anxiety, psychosis and different mood swing disorders. (Winblad 2007) Middle aged people are also faced with loss and the treatments are much the same. In a care relationship dialogue is highlighted with the treating party. (Punkanen 2001) Picture/photo therapy differs from other art therapy forms in that with pictures the client is stopped to face her past. (Mannermaa 2000, 64.) In picture therapy photographs from the client's life, symbolical pics, associative pics and new pics are used. It is also possible to combine picture therapy with other expressive therapy forms. (Halkola etc. 2009, 18) In picture therapy non professional pictures are used. Taking pictures and taken pictures can be used as therapeutic means. Picture therapy methods are often used with literature, art and music therapy. A different photographical therapy method is suitable for social-, health- and education sectors. Especially persons and entities with self-expression difficulties might benefit from the therapeutic use of photos. Visual language is the power of a photograph, it connects to feelings and experiences. Using photos it is natural to talk about and deal with difficult and sensitive issues. (Halkola et al. 2008, 9-10). Picture/Photo therapy works as other psychotherapies. The aim is to help and alleviate the client's psychological distress and symptoms and trigger a shift in mindset on the emotional and behavioral sides. In therapy the images will be discussed and pictures will be taken. A number of different ways are applied how we are in relation to the photography and picture. Individual or family pictures, old or new images, self-imposed or self imposed. In picture/photo therapy it is important that the images are figurative, as things, objects, and people or of different situations. Looking at the pictures, they bring out emotions, thoughts and images. The common denominators in creative therapies are making and expression.

The results of four studies expressed how leisure activities are a significant factor in aging well. Elderly health, functional ability, independence and experiencing quality of life all improved. (Lee etc., 2011.) By interacting with a friend positive effects can be added. It is not good to live alone. Togetherness, support of friends, appreciation are important things in a humane life. Maintaining Relationships improve quality of life. The idea with health care and nursing is to take the things which are right and do good. (Leino-Kilpi & Välimäki, 2009. 367.)

It should be noted that in Finland the elderly are not mentally as well off as often thought. Elderly Psychiatric care works, unfortunately, as a last resort and is not really a preventive mental health measure, as it was previously intended to be. (Saarenheimo 2003. 90 94) It is reasonable to consider the use of the arts and creative expressions as part of nurses working methods because the elderly psychiatric wards patients are mentally very sick. From this perspective and according to some of the ethical guidelines mentioned above as well as psychiatric cares nurses' ability, photo therapy has according to research, been able to deal with also psychologically very painful and hurtful things.

Regrettably it is clear that without early intervention regarding mental health problems among the elderly, many of them end up in psychiatric institutionalization. Early intervention can prevent problems and increase the quality of life and improve social interaction of elderly people. The forming of human relations and their maintenance is an essential part of a good old age and mental health. It lays a foundation and is also a component of good self-esteem, emotional and stress tolerance. In photo therapy, as well as in other art therapies the combining factors are active, unifying and empowering positive effects. According to these studies phototherapy and creative expressions enable reaching out to people and the evidence from using these methods are clearly positive. Using Photo Therapy could be a great way for many mentally symptomatic elderly to induce a good, intact end of life, but the supply is currently unable to meet the demand. Using photographs as a reminiscence tool is possible for anyone care worker. Photo therapy deals with using photography or photos in the therapy situation. Photo Therapy works like other psycho-therapies and is intended to alleviate the patient's psychological symptoms, and trigger a shift in thoughts, feelings and behavior. (Halkola 2009, 19-22.) Photos give people the chance to have a normal conversation within which context also painful things can be dealt with.

BRIEF SUMMARY OF THE INVENTION

In order to provide a tool for different forms of therapy and interaction, mentioned above, between the patient/client, personnel and family members a web applications is created. This web application can be used in many ways furthering wellbeing and a better health among its users as the research points out. The web application consists of 3 types of user interfaces. 1. A patient/client interface which shows, unassisted if need be, the contents that has been uploaded to it by the family members and personnel. If the patient client is more able she can also upload content to the interface. In all therapy forms and other it is of utmost importance to know the patient/client as the group presented here does. 2. A family member interface from which content can be uploaded to the patient/client interface. What family members upload appears on the patient/client interface. The contents of the patient/client interface is shared on both the family and the personnel interface forming a combined network. 3. The personnel interface from which content also can be uploaded to the shared group. The personnel interface has 2 sections the group section and then a "therapy" section to which the personnel can upload different content usable in private or group session with the patient/client. The personnel interface is divided up into many parts each part or page deals with each patient/client.

The content can be pictures, photos, films, home movies, sound and music. Music can be added with the material or separately for the patient/client to enjoy. Also speech or narrative material can be added. The 2 separate sections enable the patient/client to be part of the lives of the family members and also share events from her life independently or assisted. E.g. outings and other things can be documented and shared by the personnel bringing the elderly closer to the family members if she cannot do this herself. The other section enables a more tailored maid life cycle to be presented as well as other material usable in therapy for instance. This can be music, photos, pictures and film clips. New technology also enables drawing on tablets for instance creating an added dimension for the tool. It is easy to use and functions automatically in such a way that material uploaded is given a set time and a period during which it is presented on the interface. The same content can show from a day to a week for example depending on the amount of material that is presented on the tool. Folders for pictures, clips and music also give the personnel a perfect view into what the client likes making it beneficial for therapeutic and medical purposes as well.

The client/patient is presented with a tablet or like device with internet connection suitable for content presentation. This tablet comes with an application that regulates its on time to e.g. the day so that it functions independently presenting the material. The content i.e. pictures and clips take up the whole screen and can have writing if it is appropriate. The interface of the personnel and family members can of course be operated from any device. The material and interface form a closed circuit for the group not accessible by outsiders. Everything uploaded remains password protected and individually for each group of 3. (Patient/client, personnel and family members.)

DETAILED DESCRIPTION OF THE INVENTION

Figure 3:
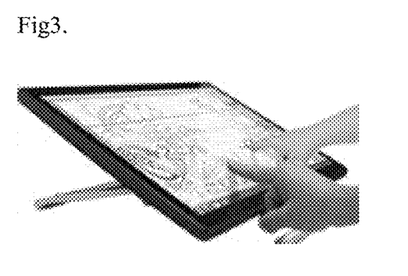
FIG. 3. Tablet or other internet connected device for the patient/client.
Figure 4:
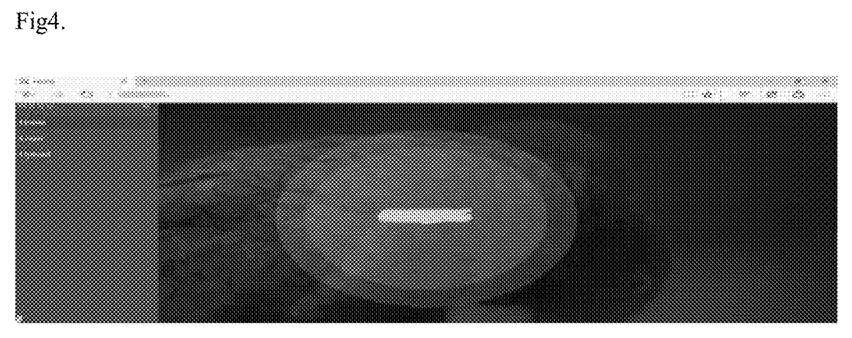
FIG. 4. Menu page.
Figure 5:
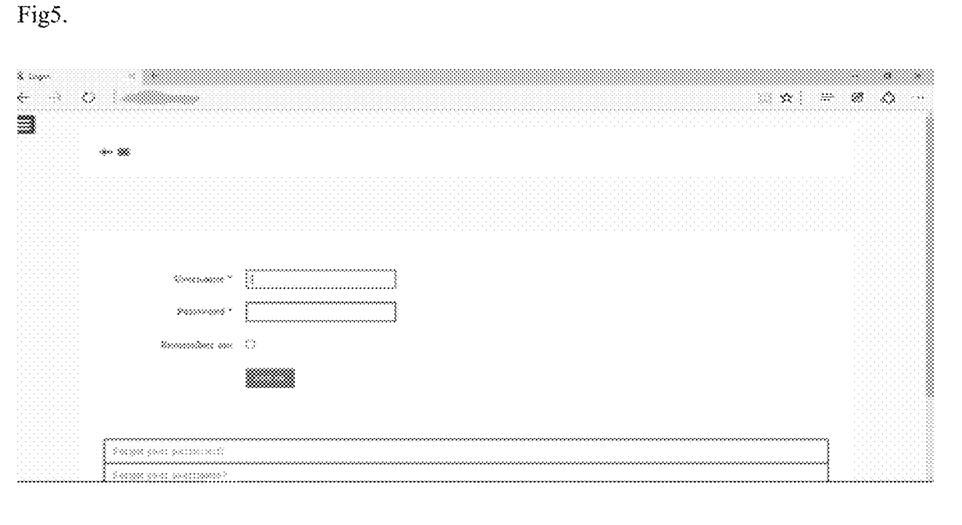
FIG. 5. Login.
Figure 6:
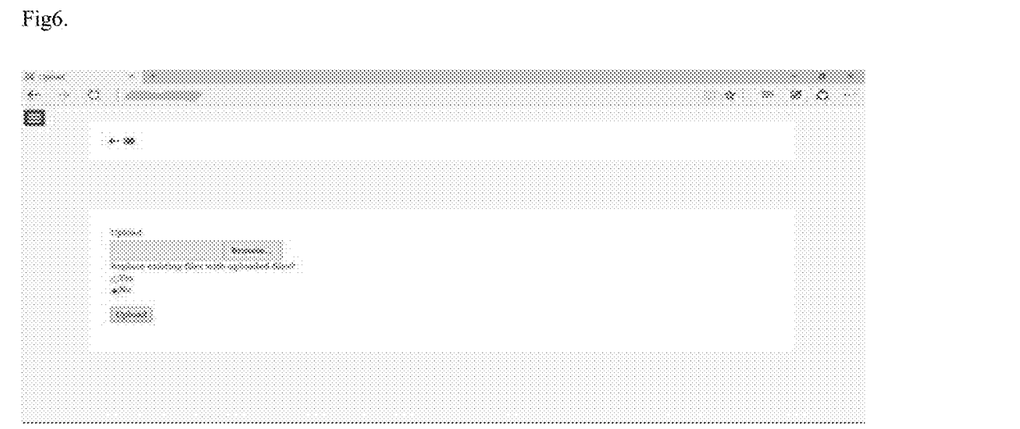
FIG. 6. Upload page for specific target.

The patient/client is given a tablet or the like on a stand so that it is kept upright. The tablet is fitted with an application controlling the "awake time" of the tablet. Thus content is rolled out according to a preset schedule from the "group" (family members, patient/client and personnel). The content is shown e.g. during the day (with the awake application) and for a set time period until substituted depending on quantity uploaded. The tablet is connected to the internet through Wi-Fi or a mobile phone connection. Content uploaded is securely stored in separate folders locally on servers or in a cloud for each client/patient. The other members of the group can of course use any device which has internet and content upload capabilities. The patient/client might also have/operate her own device. As this is a positive thing for the family members as well the costs of using this service can be shared by the family members and institution. Thus the tool becomes an inexpensive way to promote family ties, wellbeing within the group and different health and medical uses. As such it is not strain on an institutions finances on the contrary it can even be a NPV cash flow positive project in real terms.

Figure 1:
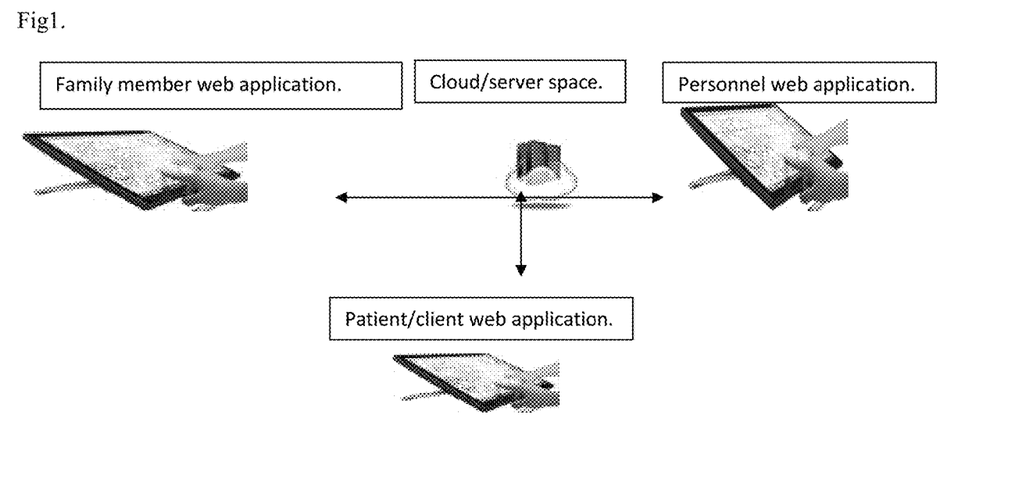
FIG. 1. System parts of the web application.
Figure 7:
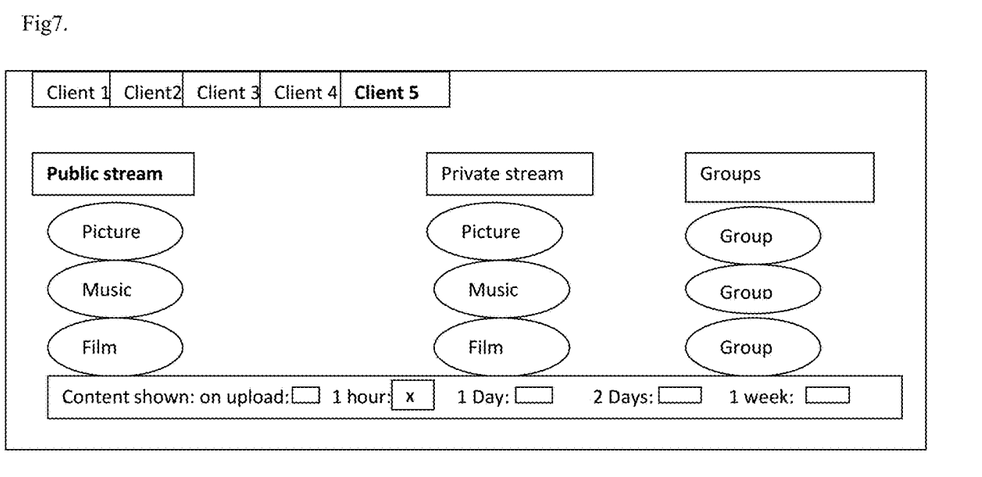
FIG. 7. Personnel view with client, public, private and group content upload. Client/patient view lacks group stream uploads and is of course individual. Timeframes depend on health condition of client. Family member view has only public stream upload function.

The web application consists of 3 types of user interfaces. 1. A patient/client interface which shows, unassisted if need be, the contents that has been uploaded to it by the family members, (patient/client) and personnel. If the patient client is more able she can also upload content to the interface. In all therapy forms and other it is of utmost importance to know the patient/client as the group presented here does. The product and framework enable this. 2. A family member interface from which content can be uploaded to the patient/ client interface. What family members upload appears on the patient/client interface. The contents of the patient/client interface is shared on both the family and the personnel interface forming a combined network. 3. The personnel interface from which content also can be uploaded to the shared group. The personnel interface has two sections the group section and then a "therapy" section to which the personnel can upload different content usable in private or group session with the patient/client. The interface is viewable through a designated internet page password protected and only accessible by the group. The personnel can then opt to show content for the patient only from the 2$^{nd}$ set of subfolders. A more able patient/client can also share content here. The personnel interface is divided up into many parts each part or page deals with each patient/client. Thus the personnel can also make joint publications to the different streams of e.g. field trips and other content interesting for all or groups of patient/clients. This also brings the family members closer to the day of the client/patient.

Figure 2:
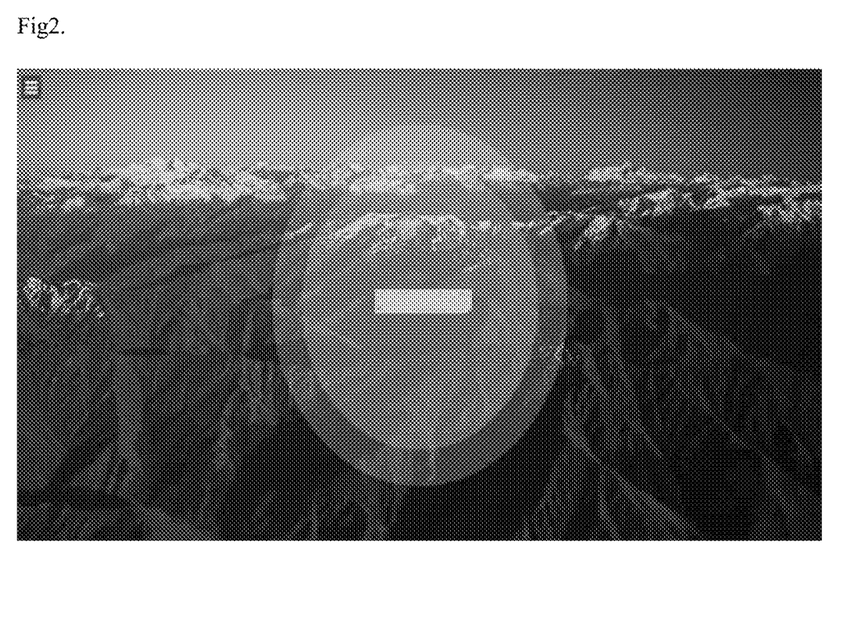
FIG. 2. The web application page. The content is only shown as large as possible for clarity. The content rolls at a set pace.

The content can be pictures, photos, films, home movies, sound and music. Music can be added with the material or separately for the patient/client to enjoy. Knowing the client is essential here. Also speech or narrative material can be added. The 2 separate sections enable the patient/client to be part of the lives of the family members and also share events from her life independently or assisted. E.g. outings and other things can be documented and shared by the personnel bringing the elderly closer to the family members if she cannot do this herself. The other section enables a more tailored maid life cycle to be presented as well as other material usable in therapy for instance. This can be music, photos, pictures and film clips. New technology also enables drawing on tablets for instance creating an added dimension for the tool. It is easy to use and functions automatically in such a way that material uploaded is given a set time and a period during which it is presented on the interface. The same content can show from a day to a week for example depending on the amount of material that is presented on the tool. Folders for pictures, clips and music also give the personnel a perfect view into what the client likes making it beneficial for therapeutic and medical purposes. The personnel can use client material in private session and other therapy like music, picture and movie therapy. As the personnel can access material for groups of client/patients the tool is suitable for group work as well. Naturally all music for medical purposes require knowledge and material of the patient/client presented here.

The invention claimed is:

1. A method, creating therapies, automatically for a patient, and for his or her family, enabling interaction for a user group consisting of a patient, his or her family and personnel in health care and elderly care, comprising:

providing a display device with display with internet connection and an interface or application controlling the on time for said patient in a patient care place with a web based application, forming a combined network consisting of 3 types of user interfaces, said user group folders for chosen content uploading on said combined network of a personnel interface, a patient interface and a family interface on which chosen and uploaded said user group folder content is shared viewable through designated internet pages, connected to local servers or cloud servers, individually password-protected for each said user group, functioning on any one of a computer, tablet or display device with internet connection, sharing in a stream chosen and uploaded content of pictures, drawings, pictures with writing, writing, moving pictures or movies, sound, music, speech and narrative material and medical material for said patient and to its users and said user group that control said 3 types of user interfaces;

providing said web based application with said patient interface for said display device with display connected to a private folder for said chosen and uploaded content by said patient and said personnel, forming said combined network on which said chosen and uploaded content is shared through said designated internet page by said web based application on said display device with display for said patient, and said web based application with said patient interface for said display device with display connected to a public folder for said chosen and uploaded content by said patient, said family and said personnel, forming said combined network on which said chosen and uploaded content is shared through said designated internet page by said web based application on said display device with display for said patient;

providing said web based application with said family interface functioning on said any one of a computer, tablet or display device connected to said public folder for said chosen and uploaded content by said family, said patient and said personnel, forming said combined network on which said chosen and uploaded content is shared through said designated internet page by said web based application, functioning on said any one of a computer, tablet or display device for said family;

providing said web based application with said personnel interface functioning on said any one of a computer, tablet or display device connected to said public folders for all said user groups for said chosen and uploaded content by said personnel, said family and said patient, forming said combined network on which said chosen and uploaded content is shared through said designated internet page by said web based application, functioning on said any one of a computer, tablet or display device for said personnel, and to said private folders for all said patients and said personnel for said chosen and uploaded content by said personnel, and said patient, forming said combined network on which said chosen and uploaded content is shared through said designated internet page by said web based application, functioning on said any one of a computer, tablet or display device for said personnel;

providing said interface of said web based application and said display device with display controlling said on time turning it on or off;

providing said web based application with said family interface, said patient interface and said personnel interface with said designated internet pages with said individual password protection for said user group stored on said local servers or cloud servers;

providing, by said user group, said chosen and uploaded content in said public folder;

providing, by said user group, said medical material chosen and uploaded for said user group in said user group's folders;

providing, by said patient and said personnel, said chosen and uploaded content in said private folder.

2. Method of claim 1, wherein said local servers or cloud servers linked to said web based application and said display device with display, store said chosen and uploaded content that said web based application used on said user group devices share in a stream based upon the user interface and its password, until it is substituted by said users, so that said chosen and uploaded content to said public folder of said family interface is shared in a stream among said combined network of said patient interface and said personnel interface belonging to said family's interface;

said chosen and uploaded content to said public folder or said private folder on said patient interface is either shared in a stream, using said public folder, among said combined network of said personnel interface and said family interface belonging to said patient's interface or,
shared in a stream, using said private folder, among said combined network of said personnel interface belonging to said patient's interface; and said chosen and uploaded content to said public folder or said private folder for each said patient on said personnel interface is either shared in a stream, using said public folder, among said combined network of said patient interface and said family interface belonging to said personnel's interface or,
shared in a stream, using said private folder, among said combined network of said patient interface belonging to said personnel's interface.

3. Method of claim 1, wherein said display device with display with said web based application form for said patient and his or her said family their individual said user interfaces with password protection accessible through said designated internet pages; and said personnel have their individual said user interface with password protection linked to their said user groups, accessible through said designated internet page.

4. Method of claim 1, wherein said interface allows said on time to be set either in said personnel interface or said user interfaces, so that said chosen and uploaded content is presented in a stream to said patient in said patient care place via said display device with display;

said display device with display associated with said patient has said application controlling its said on time, turning it on and presenting in a stream said patient's interface said chosen and uploaded content at set time intervals and then turning it off; and said display device with display is provided with a stand in said patient care place.

5. A display device with display with internet connection and with a stand to said display device with display and an interface or application controlling the on time in a patient care place with a web based application with 3 user interfaces, user group folders for chosen content uploading on a patient interface, a personnel interface and a family interface, forming a combined network on which uploaded said user group folder content is shared accessible through designated internet pages creating therapies, automatically for a patient, and for his or her family, and enabling interaction between said 3 user interfaces that can be documented in health care and elderly care, comprising:

said patient said display device with display with said stand and said internet connection and said interface or application controlling said on time capable of connecting to the internet, running said patient interface internet page through said web based application that shares in a stream the content of user supplied pictures, drawings, pictures with writing, writing, moving picture or movies, sound, music, speech and narrative material and medical material from said combined network of said 3 user interfaces;

said web based application includes said interface and said display device with display includes said application for controlling said on time, turning it on or off at set times;

said web based application forms 3 individually password-protected said patient interface, said family interface and said personnel interface accessible through said display device with display and said designated interface internet pages,
said patient interface, said family interface and said personnel interface form said combined network with a public folder set for uploading said content;

said patient interface and said personnel interface form a combined network in said combined network and contain a private folder set for uploading said content until substituted by its users;

said personnel interface contains said public and said private folder sets, forming a combined network in said combined network, for uploading said content for all said patient interfaces and said family interfaces using said web based application;

said display device with display include a function for adding writing and drawings to said content;

said music can be added with said content or separately and said narrative material can be added to said content using said web based application;

all interfaces include said interface function for setting said patient interface's said content said on time, turning said designated internet pages on or off at set times;

said web based application shares said content in a stream, until it is substituted by its users, from said public folder set, on said patient display device with display's interface internet page and on that patient's family interface and personnel interface internet pages;

said web based application shares said content in a stream, until it is substituted by its users, from said private folder set on said patient display device with display's interface internet page and on that patient's personnel interface internet page, when chosen;

said web based application is accessible through the internet.

* * * * *